United States Patent [19]

Iimuro et al.

[11] Patent Number: 5,248,839
[45] Date of Patent: Sep. 28, 1993

[54] PREPARATION PROCESS OF BISPHENOL A

[75] Inventors: Shigeru Iimuro, Aichi; Akira Yamada; Kenichi Ohmura, both of Kanagawa; Toshio Houri, Osaka; Tsuguo Kawamura, Chibe, all of Japan

[73] Assignee: Mitsui Toatsu Chemicals, Inc., Tokyo, Japan

[21] Appl. No.: 846,997

[22] PCT Filed: Aug. 15, 1991

[86] PCT No.: PCT/JP91/01083
§ 371 Date: Apr. 7, 1992
§ 102(e) Date: Apr. 7, 1992

[87] PCT Pub. No.: WO92/03399
PCT Pub. Date: Mar. 5, 1992

[30] Foreign Application Priority Data

Aug. 21, 1990 [JP] Japan .................... 2-218113
Aug. 21, 1990 [JP] Japan .................... 2-218114

[51] Int. Cl.⁵ .................................... C07C 37/20
[52] U.S. Cl. .......................... 568/727; 568/722; 568/728
[58] Field of Search ............. 568/727, 723, 722, 728

[56] References Cited

U.S. PATENT DOCUMENTS

| | | | |
|---|---|---|---|
| 2,730,553 | 1/1956 | Williamson | 568/727 |
| 4,935,553 | 6/1990 | Iimuro et al. | 568/727 |
| 4,946,877 | 8/1990 | Iimuro et al. | 568/727 |
| 4,954,661 | 9/1990 | Iimuro et al. | 568/727 |

FOREIGN PATENT DOCUMENTS

1-180843 7/1989 Japan .................... 568/727

Primary Examiner—Werren B. Lone
Attorney, Agent, or Firm—Burns, Doane, Swecker & Mathis

[57] ABSTRACT

A preparation process of high purity bisphenol A from phenol and acetone with a continuous or batch type reactor by on-line estimating with a computer the composition of the reaction mixture and saturated dissolving temperature of bisphenol A under the reaction conditions and by automatically controlling the reaction conditions and liquid transfer conditions of the reaction mixture to the next step. The process does not form crystals of bisphenol A-phenol adduct in the reactor and cooler. A maximum rate of reaction can be obtained. Consequently, fluctuation of reaction temperature can be prevented and the amount of impurities formed is small. The discharge operation of the reaction mixture from the reactor can be carried out steadily and with ease, and does not disturb the operation of successive steps.

5 Claims, 5 Drawing Sheets

PREPARATION PROCESS OF BISPHENOL A

BACKGROUND OF THE INVENTION

1. Field of the Invention

The present invention relates to a method for controlling reaction conditions and liquid transfer conditions in the preparation of bisphenol A by reacting phenol with acetone. More particularly, the invention relates to a preparation process of high-purity bisphenol A by controlling the reaction conditions in the reaction of phenol with acetone through the on-line estimation of a computer of the composition of the reaction mixture, the saturated solubility of bisphenol A and the slurry concentration of the adduct of bisphenol A with phenol (hereinafter refferred to as bisphenol A-phenol adduct) in the reactor, and further controlling the liquid transfer conditions of the resulting reaction mixture to the next step.

2. Description of the Related Art

There has been an increased demand for bisphenol as a material for engineering plastics in addition to polycarbonate resin and epoxy resin. Colorless and high purity bisphenol A is required for these uses.

In a process for preparing high purity bisphenol A, for example, phenol is reacted with acetone in the presence of an acid catalyst, and the reaction product is treated to remove the catalyst, water and a small amount of phenol. The residual liquid mixture is cooled to crystallize bisphenol A in the form of a phenol adduct, precipitated crystals are separated from the mother liquor, and phenol is removed from the bisphenol A adduct to recover bisphenol A.

Japanese Laid-Open Patent Hei 01-180843 has disclosed a process for reacting phenol and acetone in a continuous type reactor, completely reacting the reaction mixture which contains unreacted acetone in the presence of an hydrochloric acid catalyst in a batch type reactor so as to decrease unreacted acetone to substantially zero, and thereafter treating the reaction product in a purification step.

The process carries out the reaction to form minimum amounts of by-products and impurities, and makes a post-treatment step as simple as possible to prepare high-purity bisphenol A. However, no disclosure is found on the realtime analyzing and controlling method required for carrying out the process.

In cases of conducting the reaction through two steps composed of continuous and batch type reactors, an important and difficult technique is how to maintain the command on the reaction system which is continuously affected by the changing operational environment and disturbances.

As a practical problem, for example, when the reaction has progressed exceeding the set point in the first step in the continuous type reactor, bisphenol A-phenol adduct crystallizes in said reactor and it becomes difficult to transfer the reaction mixture to the second step in the batch type reactor. Further, when the heat of reaction is removed by an external heat exchanger, crystals of said adduct severely decrease the heat transfer efficiency of the heat exchanger and therefore increase the reaction temperature. As a result, by-products and impurities are formed in large amounts, which increased, lead to separation cost for these substances in the post treatment step, and result in a decrease of the purity of the product bisphenol A. In the worst case, operation of the whole production steps must be stopped.

On the other hand, when the set point in the first step reaction is low in order to avoid the above problems, the reaction time in the batch type reactor of the second step increases, requires scale up of said reactor and leads to a severe reduction of production efficiency. In order to solve these problems, it is important to prescribe suitable set points and to carry out rapid and adequate control on the rate of reaction so as to always coincide practical operating conditions with the set points.

In order to conduct adequate control, it is required to know the reaction rate in every second within a short time. The rate of reaction is affected by various factors such as the raw materials phenol and acetone, catalyst hydrochloric acid, formed bisphenol A and water, by-products and impurities. These substances form three phase equilibrium in vapor-liquid-solid and it is hence very difficult to always manage and control the rate of reaction.

After finishing the reaction in the second step batch type reactor, the resulting slurry of the reaction mixture is continuously transfered to a dehydrochlorination column in order to distill off hydrogen chloride and water from said reaction mixture. In the course of transfer, another problem develops. A buffer tank is usually employed for transferring the slurry from the batch type reactor to a continuous post treatment step. Discharge of the reaction mixture from the batch type reactor to the buffer tank is carried out intermittently at a constant interval in usual cases, at a different interval in some cases. The reaction mixture in the buffer tank is continuously fed to the dehydrochlorination column. The composition of the reaction product slurry and concentration of the slurry must be as constant as possible. Variation of these factors in the dehydrochlorination column disturbs the distribution concentration in the direction of height and causes a fluctuation in the amount of distillation. As a result, the internal pressure of the column changes and the slurry encounters increases in the variation of concentration distribution, thereby provides an increase in the residual hydrogen chloride in the liquid discharged from the column, gives adverse effects on the equipment in the next separation and purification step, and leads to serious deterioration of hue which is the most important characteristic of the product bisphenol A.

On the other hand, when an excess amount of phenol is always fed to the liquid transfer line, or an excess amount is distilled out of the dehydrochlorination column in order to prevent the above problems, phenol is distilled in excess with hydrogen chloride and water, and an increased amount of phenol circulates in the system. As a result, utility costs become too high, excess facility is required for preventing discharge of phenol out of the system, and hence productivity of bisphenol A is severely impaired.

In order to maintain the composition of the reaction mixture or the slurry concentration of bisphenol A-phenol adduct at a constant level, it is required to understand within a short time the material balance in view of the variation of said composition due to the reaction in the batch type reactor or the buffer tank, the amount of phenol required for washing the batch type reactor, and the amount of phenol required for purging the level gauge.

The rate of reaction in the batch type reactor and the buffer tank can only be estimated by considering the composition of a mixture which is fed to said batch type reactor at the start of the reaction, the reaction temperature which varies with time during the reaction, and the three phase equilibrium of vapor-liquid-solid formed by the reaction mixture. However, it is very difficult to always manage and control these factors.

Accordingly, the objects of the present invention are to solve the above problems in the preparation of bisphenol A from phenol and acetone and to provide a process for preparing high purity bisphenol A by conducting reaction control and liquid transfer control of the reaction mixture under stable conditions.

SUMMARY OF THE INVENTION

As a result of an intensive investigation in order to accomplish the above objects, the present inventors have found that the above objects can be achieved by on-line estimation with a computer of the composition of a reaction mixture and the saturated solubility temperature of bisphenol A under reaction conditions in reacting phenol with acetone in a continuous or batch type reactor and thereby automatically controlling the reaction conditions and the liquid transfer conditions of the reaction mixture to the next step. Thus the present invention has been completed.

That is, one aspect of the present invention is a preparation process of bisphenol A from phenol and acetone in the presence of an acid catalyst; and more particularly, is a preparation process of bisphenol A from phenol and acetone in the presence of an acid catalyst with a production system which includes (1) ① a continuous-flow type reactor equipped with lines for individually feeding raw materials, a catalyst and circulating liquid, means for controlling the interior and jacket temperatures of the reactor, and a discharge line of a reaction mixture or ② a continuous-flow type reactor equipped with lines for individually feeding raw materials, a catalyst and circulating liquid, means for controlling the interior and jacket temperatures of the reactor, an external circulation line and heat-exchanging means for cooling the reaction mixture by circulating the reaction mixture outside the reactor, and a discharge line of the reaction mixture, (2) a batch type reactor equipped with a feed line of the reaction mixture containing bisphenol A which is formed by reaction of phenol with acetone and discharged from the continuous-flow type reactor, means for controlling the interior temperature and a level gauge on the reactor, a feed line for purge phenol for the level gauge, and a discharge line of a reaction mixture, ③ a buffer tank equipped with lines for individually feeding the reaction mixture discharged from said batch type reactor, washing phenol and purge phenol for a level gauge and ④ a dehydrochlorination column equipped with a line for transfer-feeding the reaction mixture existing in said buffer tank and a line for feeding additional phenol, comprising:

(a) in the production system including the above continuous-flow type reactor, inputting to a computer, through a detector and a signal circuit which are mounted on the production system, operating conditions on ① flow rates of the raw materials, catalyst and circulating liquid which are fed to the continuous-flow type reactor and composition of said circulating liquid, and ② level and temperature of the reaction mixture in said reactor; estimating ③ the composition of the reaction mixture, saturated solubility of bisphenol A, and slurry concentration of bisphenol A-phenol adduct through a calculating mechanism of the computer; comparing ④ these estimates with prescribed set points; and controlling the rate of feeding the raw materials and catalyst to said reactor and the rate of discharging the reaction mixture from said reactor so as to prevent crystallization of said adduct in said reactor, or so as to prevent an increase in the slurry concentration exceeding the prescribed level:

(b) in the production system including the continuous-flow type reactor equipped with a heat exchanger for externally circulating and cooling the reaction mixture, inputting to a computer, through a detector and a signal circuit which are mounted on the production system, operating conditions on ① flow rates of the raw materials, catalyst and circulating liquid which are fed to the continuous-flow type reactor and composition of said circulating liquid, ② level and temperature of the reaction mixture in said reactor, and additionally ③ flow rate and temperature of cooling water which is fed to said heat exchanger and of the reaction mixture which is circulated to said heat exchanger; estimating ④ the composition of the reaction mixture, saturated dissolution temperature of bisphenol A and slurry concentration of bisphenol A-phenol adduct in said reactor and said heat exchanger through a calculating mechanism of the computer; ⑤ comparing these estimates with prescribed set points; controlling the rate of feeding the raw materials and catalyst to said reactor and the rate of discharging the reaction mixture from said reactor so as to prevent crystallization of said adduct in said reactor or so as to prevent an increase in the slurry concentration exceeding the prescribed level; and controlling the heat-removing rate from the heat exchanger so as to maintain the temperature of the reaction mixture above the saturated dissolution temperature or the super saturation temperature of bisphenol A:

(c) in the above batch type reactor, ① inputting to the computer the composition and temperature of the raw material mixture which is fed to said batch type reactor through a detector and a signal circuit which are mounted on the production system; ② calculating time dependent variation of the reaction mixture composition in said reactor with a numerical integration method; ③ estimating the composition of the reaction mixture and slurry concentration of bisphenol A-phenol adduct at the end of the reaction through a calculating mechanism of the computer; ④ comparing these estimates with prescribed set points; and controlling the concentration of said slurry by adjusting the flow rate of additional phenol so as to stabilize the composition of said reaction mixture or the concentration of said slurry which is continuously fed from a reaction step to a dehydrochlorination step:

(d) in a preparation process of bisphenol A which is carried out by a combination of (a) and (c), or (b) and (c), practically, in a preparation process of bisphenol A from phenol and acetone in the presence of an acid catalyst with a production system which includes the above continuous-flow type reactor, batch type reactor, buffer tank and dehydrochlorination column, a first step of inputting to the computer, through a detector and a signal circuit which are mounted on the production system, operating conditions on ① flow rates of the raw materials, catalyst and circulating liquid which are fed to the continuous-flow type reactor and composition of said circulating liquid, ② the level and temperature of the reaction mixture in said reactor, and ③ temperature of the reaction mixture in the batch type reactor; estimating ④ the composition of the reaction mixture, saturated solubility of bisphenol A and slurry concentration of bisphenol A-phenol adduct in the continuous-flow type reactor through a calculating mechanism of the computer; comparing ⑤ these estimates with prescribed set points; and thereby controlling the rate of feeding the raw materials and catalyst to said reactor and the rate of discharging the reaction mixture from said reactor so as to prevent crystallization of said adduct in said reactor or so as to prevent an increase in the slurry concentration exceeding the prescribed level; and a second step of ⑥ inputting to the computer the temperature of the reaction mixture in said batch type reactor; ⑦ calculating time dependent variation of the reaction mixture composition in said reactor with a numerical integration method; ⑧ estimating the composition of the reaction mixture and slurry concentration of bisphenol A-phenol adduct at the end of the reaction through a calculating mechanism of the computer; ⑨ comparing these estimating with prescribed set points; and controlling the concentration of said slurry by adjusting the flow rate of additional phenol so as to stabilize the composition of said reaction mixture or the concentration of said slurry which is continuously fed from a reaction step to a dehydrochlorination step: and (e) in a preparation process of bisphenol A from phenol and acetone in the presence of an acid catalyst with a production system which includes the above continuous-flow type reactor having an external circulation line, batch type reactor, buffer tank and dehydrochlorination column, a first step of inputting to the computer, through a detector and a signal circuit which are mounted on the production system, operating conditions on ① flow rates of the raw materials, catalyst and circulating liquid which are fed to the continuous-flow type reactor and a composition of said circulating liquid, ② the level and temperature of the reaction mixture in said reactor, and ③ the flow rate and temperature of cooling water which is fed to said heat exchanger and of the reaction mixture which is circulated to said heat exchanger; estimating ④ the composition of the reaction mixture, saturated solubility of bisphenol A and slurry concentration of bisphenol A-phenol adduct in said reactor through a calculating mechanism of the computer; ⑤ comparing these estimates with prescribed set points; and thereby controlling the rate of feeding the raw materials and catalyst to said reactor and the rate of discharging the reaction mixture from said reactor so as to prevent crystallization of said adduct in said reactor or so as to prevent increase in the slurry concentration exceeding the prescribed level and also controlling the heat-removing rate from said heat exchanger so as to maintain the temperature of the reaction mixture above the saturated solubility temperature or supersaturated solubility temperature of bisphenol A; and further a second step of ⑥ inputting to the computer the temperature of the reaction mixture in said batch type reactor; ⑦ calculating time dependent variation of the reaction mixture composition in said batch type reactor with a numerical integration method; ⑧ estimating the composition of the reaction mixture and slurry concentration of bisphenol A-phenol adduct at the end of the reaction through a calculating mechanism of the computer; ⑨ comparing these estimates with prescribed set points; and thereby controlling the concentration of said slurry by adjusting the flow rate of additional phenol so as to stabilize the composition of said reaction mixture or the concentration of said slurry which is continuously fed from a reaction step to a dehydrochlorination step.

By carrying out the reaction according to the process of the invention, a maximum rate of reaction can be obtained while preventing crystal formation of bisphenol A-phenol adduct from the reaction mixture. Even though the reaction mixture is cooled by using an external cooler in the course of the reaction, bisphenol A-phenol adduct does not form crystals in the cooler. Consequently, fluctuation of reaction temperature can be prevented and the amount of impurities formed is decreased. Discharge of the reaction product from the reactor can be steadily carried out with ease and does not disturb the operation in the next step.

Even in the case of intermittently discharging the reaction mixture from the batch type reactor to the buffer tank after finishing the reaction, the composition of the reaction mixture which is fed to the continuously operating dehydrochlorination column can be controlled to the set point. Thus, operating conditions of the dehydrochlorination column are not disturbed and high purity bisphenol A can be prepared.

Figure 1:
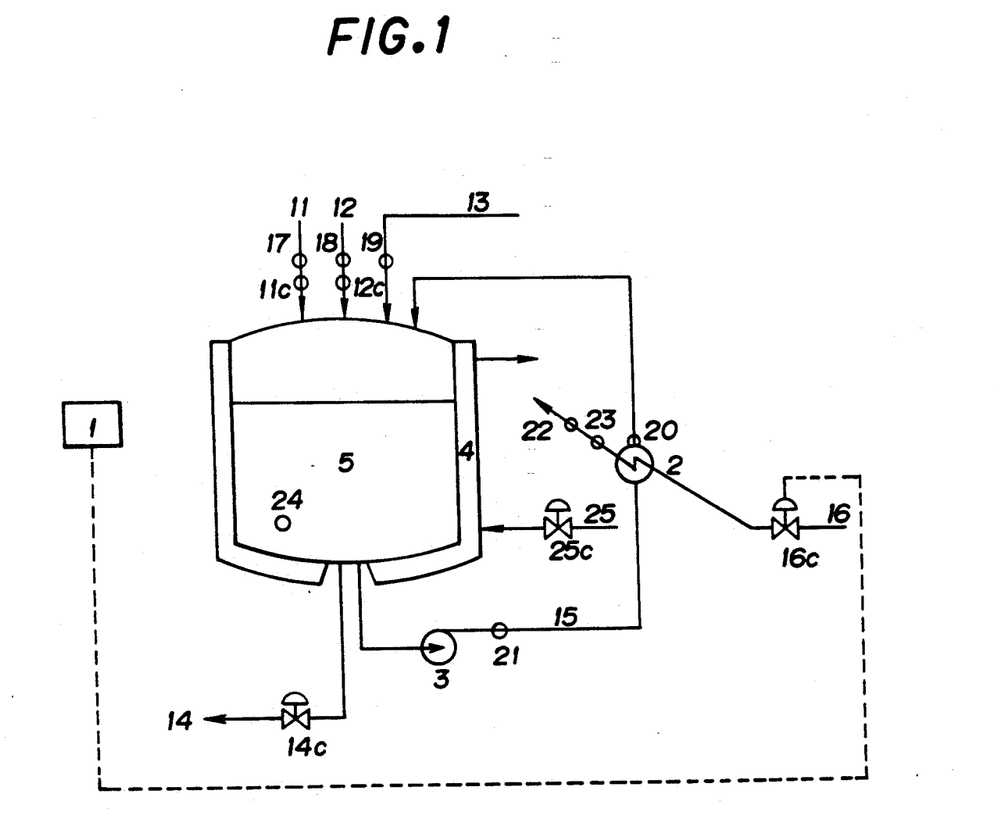
FIG. 1 is a process flow diagram illustrating an embodiment of the process of the invention by using a continuous-flow type reactor.

The figures in FIG. 1 individually indicate the following instruments.

Figure 4:
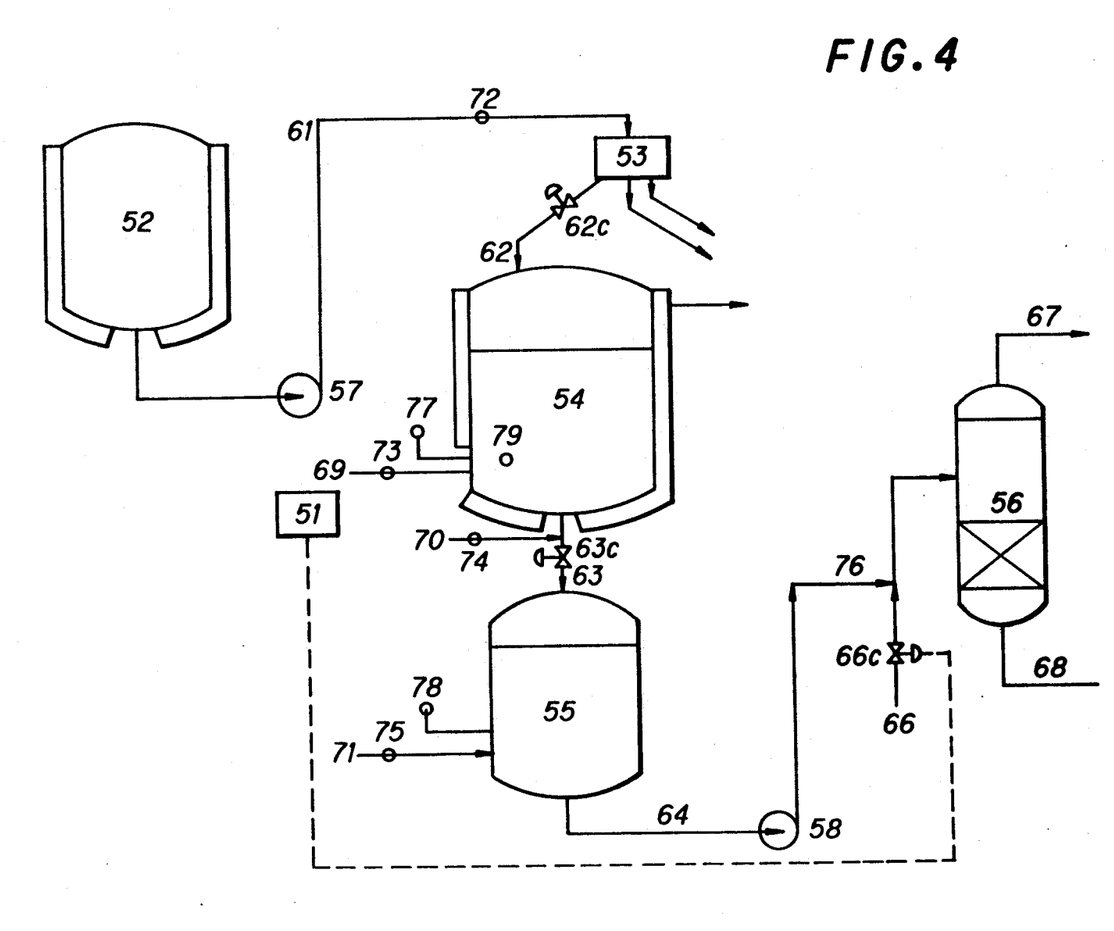
FIG. 4 is a process flow diagram illustrating an embodiment of the invention by using the batch type reactor.

1—Computer
2—External heat exchanger
3—Reaction mixture external circulation pump
4—Reactor jacket
5—Reactor
11—Raw material feed line
12—Catalyst feed line
13—Circulating liquid feed line
14—Reaction mixture discharge line
15—Reaction mixture external circulation line
16—Cooling water line
17—Feeding material flow meter
18—Feeding catalyst flow meter
19—Circulation liquid flow meter
20—External circulation liquid thermometer
21—External circulation liquid flow meter
22—Cooling water flow meter
22—Cooling water flow meter
23—Cooling water thermometer
24—Reactor thermometer
25—Jacket cooling water line
11c—Raw material feed valve
12c—Catalyst feed valve
14c—Reaction mixture discharge valve
16c—Cooling water valve
25c—Jacket cooling water valve The figures in FIG. 4 individually indicate the following instruments.

51—Computer
52—Continuous-flow type reactor
53—Liquid distributor

54—Batch type reactor
55—Buffer tank
56—Dehydrochlorination column
57, 58—Pump
61—Reaction mixture transfer line
62—Reaction mixture charge line
63—Reaction mixture discharge line
64—Reaction mixture feed line
66—Additional phenol feed line
66c—Additional phenol control valve
67—Dehydrochlorination column gas discharge line
68—Dehydrochlorination column liquid discharge line
69,71—Level gauge purge phenol line
70—Washing phenol line
72—Reaction mixture flow meter
73,75—Purge phenol flow meter
74—Washing phenol flow meter
76—Dehydrochlorination column feed line
77—Batch type reactor level gauge
78—Buffer tank level gauge
79—Batch type reactor thermometer
62c—Reaction mixture charge control valve

DESCRIPTION OF THE PREFERRED EMBODIMENTS

The production system used for the invention relates to a process for preparing bisphenol A from phenol and acetone in the presence of an acid catalyst.

That is, the present invention relates to a process for preparing bisphenol A from phenol and acetone in the presence of an acid catalyst with a production system which includes ① a continuous-flow type reactor equipped with lines for individually feeding raw materials, catalyst and circulating liquid, means for operating interior and jacket temperatures of the reactor, and a line for discharging a reaction mixture, or additionally an external circulation line for cooling the reaction mixture by circulating the reaction mixture outside the reactor, and heat exchanging means; ② a batch type reactor equipped with a line for feeding the reaction mixture which is discharged from said continuous-flow type reactor and contains bisphenol A formed by reaction of phenol with acetone, means for operating the interior temperature and a level gauge on the reactor, a line for feeding purge phenol to the level gage, and a discharge line of the reaction mixture; ③ a buffer tank equipped with lines for individually feeding the reaction mixture discharged from said batch type reactor, washing phenol and purge phenol for a level guage; and ④ a dehydrochlorination column connected with a line for transfer-feeding the reaction mixture discharged from said buffer tank and equipped with a line for feeding additional phenol.

The process flow diagrams which parctically illustrate the production system are shown in FIG. 1 and FIG. 4.

In FIG. 1, a mixture of phenol and acetone as the raw material and hydrogen chloride gas as the catalyst are continuously fed to the continuous-flow type reactor 5 through lines 11 and 12, respectively. A mixture composed of recovered phenol, formed water and hydrogen chloride gas is recovered as the circulating (recovery) liquid to the continuous-flow type reactor 5 through a circulating liquid feed line 13. On the other hand, the reaction mixture is discharged from a reaction mixture discharge line 14 so as to maintain a constant level in the continuous-flow type reactor 5. Heat removal from the reaction mixture is carried out with a valve 25c by controlling the amount of cooling water which circulates the reactor jacket 4. In the case of maintaining the reaction temperature at a lower level, the reaction mixture may be externally circulated through a reaction mixture external circulation line 15 and cooled by an external heat exchanger 2.

FIG. 1 illustrates a continuous-flow type reactor equipped with the external circulation line.

In FIG. 4, a reaction mixture containing unreacted acetone is discharged from a continuous-flow type reactor 52, transferred through a reaction mixture transfer line 61 and a liquid distributor 53, and successively charged from a reaction mixture charge line 62 to one or several batch type reactors 54. After a prescribed reaction time, the reaction mixture containing substantially no acetone is discharged through a reaction mixture discharge line 63 to a buffer tank 55. The reaction mixture discharged to the buffer tank 55 is continuously fed to a dehydrochlorination column 56 with a pump 58. When the reaction mixture is present, phenol for purging is supplied from a level gauge purge phenol line 69 to a level gauge 77 in order to prevent adhesion of slurry. Phenol for purging is always supplied also from a level guage purge phenol line 71 to a level guage 78 in order to prevent adhesion of slurry. When the reaction mixture is discharged to the buffer tank 55, wasining phenol is supplied from a line 70 in order to prevent blocking of the discharge line. Flow rates of purge phenol are individually measured with purge phenol flow meters 73 and 75. The flow rate of washing phenol is measured with a washing phenol flow meter 74.

The above production system is controlled by the following methods of the present invention.

In one method for controlling the continuous-flow type reactor, the concentration of bisphenol A in the reactor is on-line estimated with a computer 1 by the operation conditions such as flow rates of raw materials, catalyst and circulating liquid which are fed to the reactor and composition of said circulating liquid, and the level and temperature of the reaction mixture in said reactor, opening of the reaction mixture discharge valve 14c and/or the raw material feed valve 11c and the catalyst feed valve 12c is adjusted as control input, and the composition of the reaction mixture, concentration of bisphenol A in particular, is thereby controlled.

In another method for controlling the continuous-flow type reactor, the concentration of the reaction mixture and saturated dissolution temperature of bisphenol A are on-line estimated, in addition to the above operation conditions, by the operating conditions including the flow rate and temperature of water which is fed to said heat exchanger and the circulating amount and temperature of the reaction mixture which is circulated to said heat exchanger, opening of the reaction mixture discharge valve 14c and/or the raw material feed valve 11c and the catalyst feed valve 12c is adjusted as control input and composition of the reaction mixture, concentration of bisphenol A in particular, is thereby controlled, and the heat-removing rate from said heat exchanger is controlled by adjusting opening of the cooling water valve 16c as control input.

In a further method for controlling the batch type reactor, time dependent variation on the composition of the reaction mixture in said reactor is calculated with a numerical integration method from a composition of the reaction mixture which is fed to said reactor and the temperature of said reactor, amounts of washing phenol and purge phenol are input to the computer, composition of the reaction mixture and slurry concentration of the bisphenol A-phenol adduct at the end of the reaction is estimated on-line with the computer, opening of valve 66c in the additional phenol feed line 66 is adjusted as control input so that the composition of the reaction mixture and the slurry concentration of bisphenol A-phenol adduct coincide with set points in the course of transferring from the reactor through the buffer tank to the dehydrochlorination column, and the composition of the reaction mixture which is fed to the dehydrochlorination column 56 is thus controlled.

The present invention which uses such a system is characterized in that, in the process for preparing bisphenol A by a one step or two step reaction using a continuous-flow type reactor and/or batch type reactor, (1) the reaction in the continuous-flow type reactor of the first step is carried out by estimating the concentration of bisphenol A in the reactor and maintaining operation conditions in the range of preventing crystallization of bisphenol A-phenol adduct, more practically, by managing and controlling the operation conditions so as to maintain the concentration of bisphenol A in the reaction mixture in the range of 10 to 25% by weight and also to maintain the reaction temperature in the range of from the saturated dissolution temperature of bisphenol A $-10°$ C. to said saturated dissolution temperature $+10°$ C. The present invention is also characterized in that (2) the reaction mixture maintaining the above estimate on the concentration of bisphenol A is fed to the batch reactor in the second step, reacted for a prescribed time, and discharged to the buffer tank; the composition of the reaction mixture and the slurry concentration of bisphenol A-phenol adduct are estimated in the course of feeding from the buffer tank to the dehydrochlorination column; and the flow rate of feeding phenol is controlled so as to meet the set points of the reaction mixture composition and the slurry concentration of bisphenol A-phenol adduct in the course of transferring from the buffer tank to the dehydrochlorination column.

An important point of the invention is the control of reaction conditions and liquid-transfer conditions. In a reaction system which is affected by constantly changing environments and disturbances, process values which cannot be directly measured with a sensor are calculated and estimated on-line, on real time and by using a model based on a solubility formula.

In cases where an external heat exchanger is installed in order to carry out heat removal from the reaction mixture in the continuous-flow type reactor, it is required to manage and control operating conditions in the location where the lowest temperature is thought to exist. The temperature in the vicinity of the wall surface which is located around the outlet of the heat exchanger and is in contact with the cooling medium, is estimated on real time in accordance with the theory of heat conduction. Thus, the object can be achieved by always maintaining the operating conditions of the reaction system including said heat exchange so as to hold said location above the crystallizing temperature of the bisphenol A-phenol adduct.

When the reaction mixture containing bisphenol A is in a supersaturated state in the reactor, the crystals of bisphenol A-phenol adduct formed, at the outlet of the external heat exchanger acts as seed crystals and crystallizes the whole reaction mixture in the reactor. The crystals are usually generated in the supersaturated state. Increased reaction temperature due to heat of formation of the crystals increases the amount of by-products and impurities. Heat energy, time and labor are required in excess in order to dissolve the generated crystals. Further, the crystals act as a factor for seriously disturbing the reaction system and leads to blocking of the liquid transfer line which moves the reaction mixture to the batch type reactor in the second step, and thus severely impairs productivity of the production system.

It is important at the end of the reaction in the batch type reactor to control the composition of the reaction mixture and the slurry concentration of bisphenol A-phenol adduct. When the reaction mixture which differs every time in composition and slurry concentration of bisphenol A-phenol adduct when the mixture is intermittently discharged from the batch type reactor to the buffer tank, the composition of the reaction mixture and the slurry concentration of bisphenol A-phenol adduct vary on being fed to the dehydrochlorination column. These are process values which cannot be directly measured with a sensor.

The present invention has enabled calculation and estimating these process values on real time, on-line and by using a model in accordance with the solubility formula.

Figure 2:
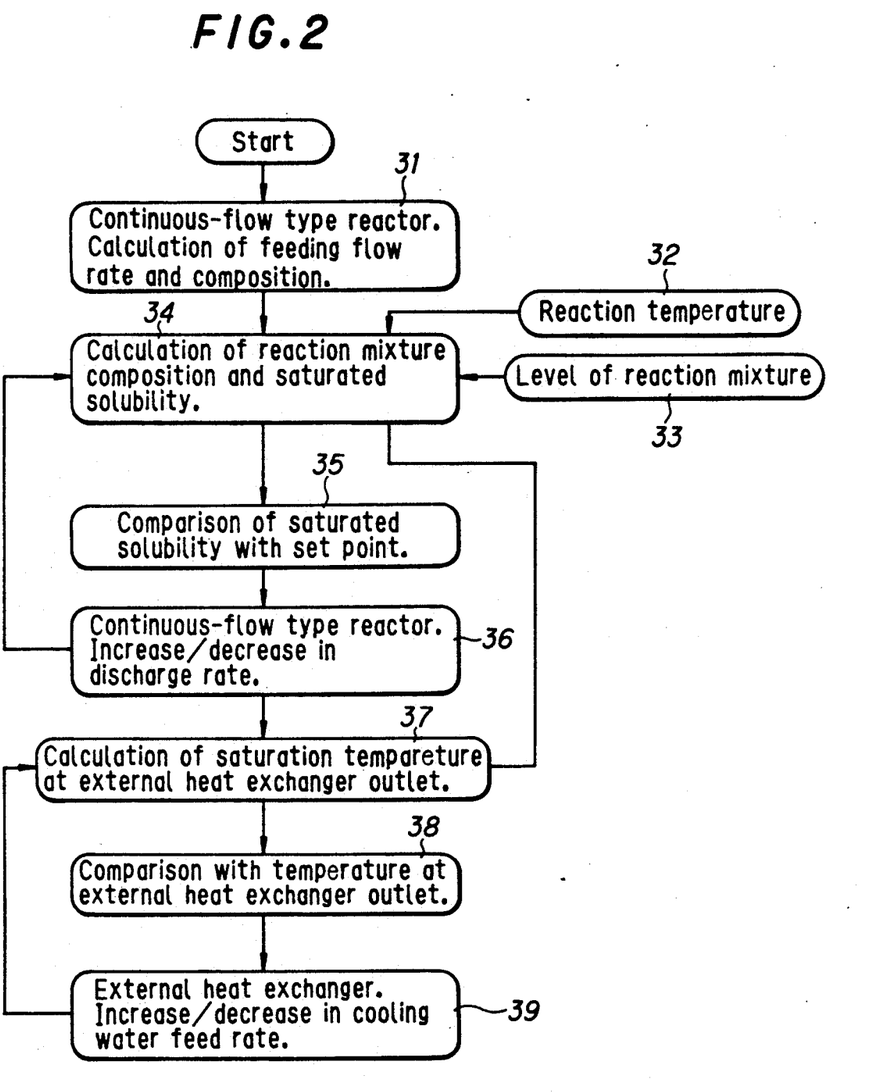
FIG. 2 is a block flow diagram illustrating an analyzing and controlling method in the continuous-flow type reactor of the invention.
Figure 5:
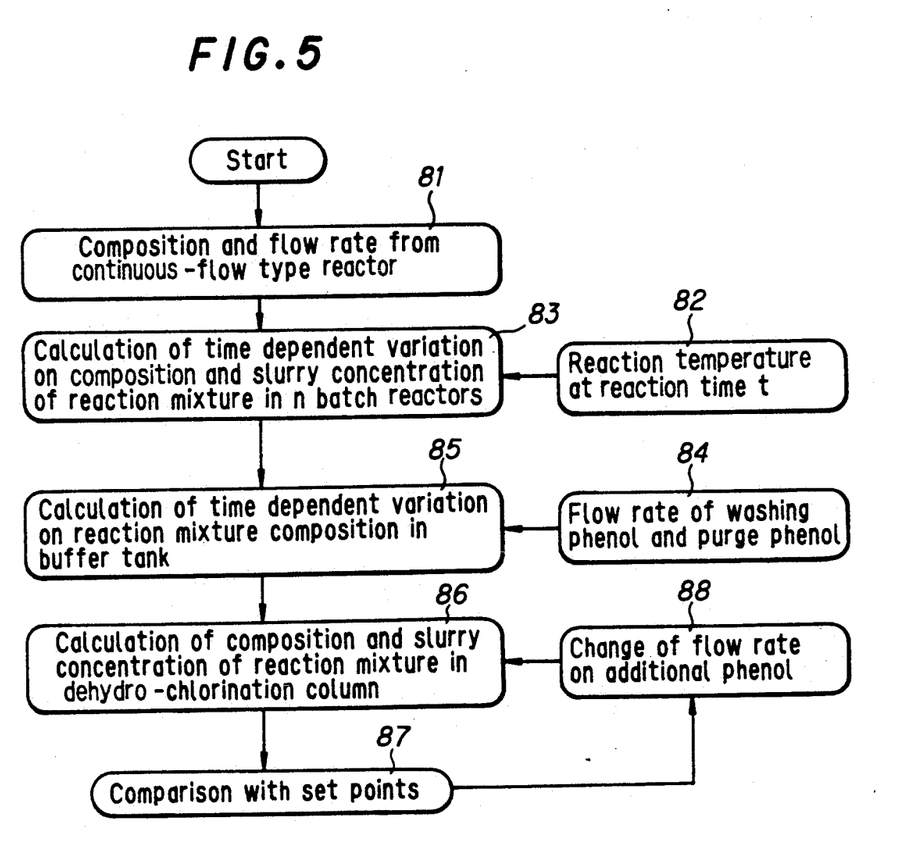

Practical controlling procedures will be demonstrated by block flow drawings of FIG. 2 and FIG. 5 which illustrate examples of the controlling method in the invention.

The block flow which illustrates practical controlling procedures in the system using the above continuous-flow type reactor is shown in FIG. 2 and has two control loops as the method for controlling the system.

In one loop, for example, in the case of obtaining a constant production rate, the raw materials and the catalyst are fixed to a constant flow rate and the flow rate of the circulating liquid is affected by the variation in successive steps. Consequently, the opening of the reaction mixture discharge valve 14c is adjusted as control input and controls the feeding rate of the raw materials and the catalyst, and composition of the reaction mixture, concentration of bisphenol A in particular.

In another loop, in the case of changing the production rate, a raw material feed valve 11c, catalyst feed valve 12c and reaction mixture discharge valve are adjusted as control input and control the composition of the reaction mixture, concentration of bisphenol A in particular.

Each flow rate of the raw materials, catalyst and circulating liquid is input on-line to the computer 1 as a signal from flow meters 17, 18 and 19, respectively. Interior temperature of the continuous-flow type reactor 5 is similarly input as a signal from a reaction mixture thermometer 24.

Figure 3:
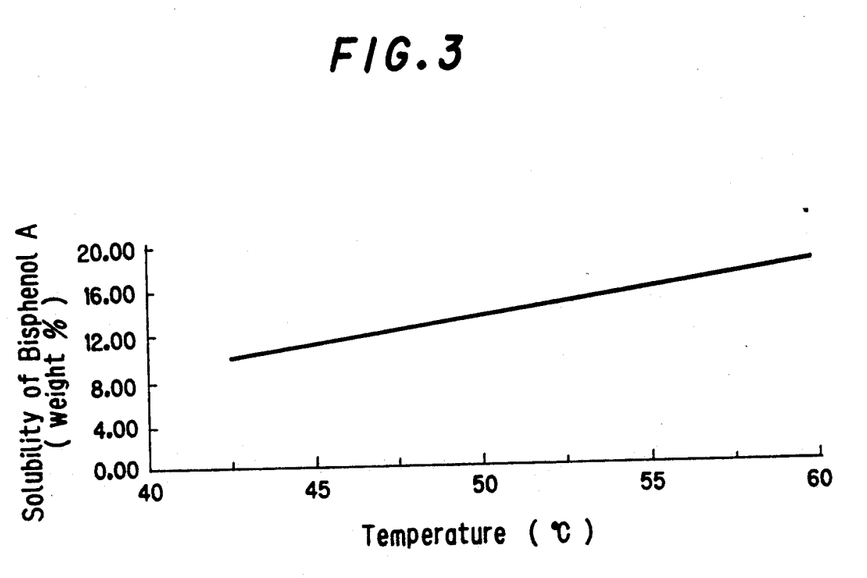
FIG. 3 is a solubility curve diagram of bisphenol A in the reaction mixture.

The flow rate of the circulating liquid fed to the continuous-flow type reactor is input as above and additionally employs as a composition a value separately estimated in the analysis of the post treatment step by the computer 1 (Steps 31, 32 and 33 in FIG. 2). Based on the above input signals, the composition of the reaction mixture can be estimated by calculating the material balance around the reactor on real time (Step 34 in FIG. 2). The above process is carried out by separately estimating on the basis of kinetic information on the bisphenol A forming reaction including side reactions and solubility of each component, for example, a solubility curve diagram in FIG. 3 and other various experimental data on phase equilibrium, and by integrating the obtained results into the computer 1 as a logic. The estimating formula used for the solubility of bisphenol A includes also solubility of the catalyst hydrogen chloride gas and other ingredients in the reaction mixture. Composition of the reaction mixture is estimated by the computer 1. The composition of the reaction mixture, saturated solubility of bisphenol A and slurry concentration of bisphenol A-phenol adduct are set so that concentration of bisphenol A is not higher than the saturated concentration or supersaturated concentration in the reaction mixture or maintains somewhat lower contraction than saturated concentration (Step 35 in FIG. 2). Control is practically carried out by the following procedures. When the concentration of bisphenol A exceeds a set point, opening of the valve 14c in the reaction mixture discharge line 14 is enlarged by the computer 1 so as to increase a discharging rate of the reaction mixture in order to lower formation rate of bisphenol A and reduce the average retention time. When the concentration of bisphenol A is lower than the set point, the reverse procedures are carried out (Step 36 in FIG. 2). Similarly, in order to increase or decrease the production rate, opening of the raw material feed valve 11c and the catalyst feed valve 12c is controlled and successively opening of a valve 14c in the reaction mixture discharge line 14 is also controlled so as to meet the circulating liquid flow rate 13 which indicates delayed variation.

In another method which uses an external heat exchanger 2, opening of the valve 16c of the cooling water which is fed through a cooling water line 16 to the external heat exchanger 2 or an external circulation flow rate 21 of the reaction mixture through a circulation pump 3 to the external heat exchanger 2 is adjusted as control input, and thus reaction mixture temperature 20 at the outlet of the external heat exchanger, preferably the temperature of a heatconducting surface of said heat exchanger is accurately controlled.

In practice, the composition of the reaction mixture in the continuous-flow type reactor 5 is estimated by the above method. Separately, the flow rate 22 and temperature 23 of cooling water which is fed to the external heat exchanger 2 and the circulating flow rate 21 and temperature 24 of the reaction mixture to the external heat exchanger 2 are input on-line to the computer 1 and heat balance around the external heat exchanger 2 is calculated in consideration of heat transfer velocity on the heat transfer surface of the external heat exchanger. The temperature of the heat transfer surface is thus estimated at the reaction mixture outlet of the external heat exchanger where the reaction mixture indicates the lowest temperature (Step 37 in FIG. 2). Supersaturated dissolution temperature, preferably saturated dissolution temperature corresponding to the reaction mixture composition which is calculated from a separately built-in estimation formula of the computer 1 is estimated as a set point (Step 38 in FIG. 2). Opening of the feed water valve 16c to the external heat exchanger 2 is thus controlled so as to maintain the temperature of the heat transfer surface above the set point (Step 39 in FIG. 2).

Next, FIG. 5 is a block flow drawing illustrating a practical control method in the system using a batch type reactor.

As a normal process flow, two or more batch type reactors are used to perform continuous preparation.

In order to calculate time dependent change of the reaction mixture composition and slurry concentration in the batch type reactor, the conditions at the start of charging the reaction mixture from the continuous-flow type reactor 52 to the batch type reactor 54 are automatically checked by the condition of the valve 62c, checked results are input as initial values (Step 81), and numerical integration including reaction velocity calculation is carried out in consideration of the composition and temperature of the reaction mixture (Step 83). After finishing the reaction, calculation is continued to the time when the reaction mixture is discharged from the batch type reactor and an indicated value of the level gauge 77 becomes zero.

Similarly, the buffer tank 55 is also estimated time dependent variation of the reaction mixture composition with a continuous numerical integration method (Step 85).

In order to maintain the composition or slurry concentration of the reaction mixture at the set point in the dehydrochlorination column feed line 76, the composition or slurry concentration obtained after mixing additional phenol for concentration control and the reaction mixture which is fed from the buffer tank 55 to the dehydrochlorination column 56 is calculated (Step 86), the flow rate of said additional phenol is calculated so that the concentration or slurry concentration always coincides with the set point, and opening of the valve 66c is controlled so as to maintain the thus-calculated flow rate of additional phenol (Step 87 and 88).

On carrying out the above calculation, a kinetic information on the bisphenol A preparation reaction including side reactions and phase equilibrium such as solubility of each ingredient are separately calculated on the basis of various experimental data and the results obtained are integrated into the computer 51 as a logic.

The preparation systems and the controlling methods of these systems in the present invention which are respectively illustrated above are effective in the overall system of the present invention which is obtained by combining these preparation systems. Further, combination of these preparation systems of the invention with other systems can also constitute a system which can effectively utilize the characteristics of the invention.

EXAMPLE

The present invention will hereinafter be illustrated further in detail by way of examples. Percent means percent by weight unless otherwise noted.

EXAMPLE 1

The raw materials, phenol and acetone were mixed in a mole ratio of 6:1 and continuously charged to a continuous-flow type reactor which had been previously controlled to 55° C. Into the mixture, hydrogen chloride was blown as a catalyst.

A mass flow rate of the raw materials and catalyst which were fed to the reactor, and the level and temperature of the reaction mixture in the reactor were collected on-line with a computer at a 10 second interval, the concentration of bisphenol A and other ingredients and the saturated solubility at the reaction temperature were estimated from these data, the discharge flow rate of the reaction mixture was controlled by computer output so as to obtain an average retention time which maintains the saturated solubility +2% in bisphenol A concentration, and thus the of the reactor was controlled.

The reaction mixture continuously discharged had an acetone conversion ratio of 55% and contained 3.2% of o,p'-isomer and 0.3% of Dianin's compound for the amount of bisphenol A. Liquid turbidity accompanied by crystallization of bisphenol A-phenol adduct was not observed.

COMPARATIVE EXAMPLE 1

Example 1 was carried out by manually controlling the retention time of the reaction mixture in the reactor.

As a result, crystals of bisphenol A-phenol adduct were generated in the reactor due to variation of the feed material composition. The reaction mixture became difficult to discharge from the reactor, discharging flow rate could not be controlled at a constant level, and the operation in the next step became extremely unstable.

EXAMPLE 2

The raw materials, phenol and acetone were mixed in a mole ratio of 6:1 and continuously charged to a reactor which was equipped with an external heat exchanger (cooler) and had previously been controlled to 55° C.

Hydrogen chloride was continuously blown into the mixture as a catalyst.

A mass flow rate of the raw materials and catalyst which were fed to the reactor, and the level and temperature of the reaction mixture in the reactor were collected on-line with a computer at a 10 second interval, the concentration of bisphenol A and other ingredients and the saturated solubility at the reaction temperature were estimated from these data, the discharge flow rate of the reaction mixture was controlled by computer output so as to obtain an average retention time which maintains the saturated solubility +2% in bisphenol A concentration, and thus the level of the reactor was controlled.

At the same time, the surface temperature of a heat conducting pipe at the outlet of the heat exchanger was estimated, saturated dissolution temperature of bisphenol A for the composition of the reaction mixture was estimated, and flow rate of cooling water for the external heat exchanger was controlled so as to maintain the surface temperature of the heat conducting pipe above said saturated dissolution temperature.

The reaction mixture continuously discharged had an acetone conversion ratio of 55% and contained 3.2% of o,p'-isomer and 0.3% of Dianin's compound for the amount of bisphenol A. Liquid turbidity accompanied by crystallization of bisphenol A-phenol adduct was not observed.

COMPARATIVE EXAMPLE 2

Example 2 was carried out by manually controlling the temperature at the outlet of the external heat exchanger. The reaction mixture was crystallized in the vicinity of the outlet of the external heat exchanger. The resulting crystals acted as seed crystals and crystals were also generated in the reactor.

As a result, it became difficult to discharge the reaction mixture from the reactor, discharging flow rate could not be controlled at a constant level, and the operation in the next step became extremely unstable.

EXAMPLE 3

Phenol at a flow rate of 564 kg/hr and acetone at a flow rate of 58 kg/hr were continuously mixed and charged to a continuous-flow type reactor which was maintained at 55° C. At the same time, hydrogen chloride was continuously blown into the mixture to react phenol with acetone at 55° C.

The data on the flow rates of the above raw materials and the catalyst which were continuously fed to the continuous-flow type reactor and on the temperature of the reaction mixture in the reactor were collected on-line with a computer at an interval of 10 seconds. The composition of the reaction mixture in the reactor and saturated solubility of bisphenol A or slurry concentration of bisphenol A-phenol adduct were estimated from these data.

On the bases of the above estimates, the reaction mixture was continuously discharged from said reactor so as to maintain an average retention time of 0.8 hr for the reaction mixture in the continuous-flow type reactor.

As a result, crystallization of bisphenol A-phenol adduct in said reactor was not observed. Acetone conversion rate was 25%.

Next, said reaction mixture was charged to a batch reactor having a content volume of 1.2 $m^3$ during 1.2 hours and reacted for 9 hours with stirring under blowing of hydrogen chloride gas. After finishing the reaction, the reaction mixture was discharged into a buffer tank having a content volume of 1.5 $m^3$. The reaction mixture in the buffer tank was continuously fed to a dehydrochlorination column at a flow rate of about 650 kg/hour.

At this time, the process values of flow rate, temperature, level and opening signal of a liquid transfer valve around the batch reactor and buffer tank were collected on-line with a computer at an interval of 10 seconds.

The composition and slurry concentration of the reaction mixture at the end of the reaction in the batch reactor were calculated on-line on the basis of these data. Based on the calculation results, the flow rate of additional phenol was controlled so as to maintain the concentration of bisphenol A in the feeding line to the dehydrochlorination column at a constant level of 28% by weight. The average flow rate of additional phenol was 40 kg/hr. As a result of quantitative analyses by sampling every 10 minutes, the hydrogen chloride concentration of dehydrochlorination column discharge liquid was 3 to 10 ppm.

COMPARATIVE EXAMPLE 3

Example 3 was carried out by continuously feeding additional phenol to the dehydrochlorination column feed line at a constant flow rate of 40 kg/hr without controlling the flow rate so as to obtain the bisphenol A concentration of about 28% by weight.

As a result of quantitative analyses by sampling every 10 minutes, the hydrogen chloride concentration of the dehydrochlorination column discharge liquid was 5 to 43 ppm. Thus, the dehydrochlorinated reaction mixture had a higher content of residual hydrogen chloride as compared with that of Example 3. Red brown color was observed on the reaction mixture obtained.

We claim:

1. A preparation process of bisphenol A from phenol and acetone in the presence of hydrogen chloride as an acid catalyst with a production system which includes a continuous-flow type reactor equipped with lines for individually feeding raw materials, catalyst and circulating liquid, means for controlling the interior and jacket temperatures of the reactor by controlling process conditions so as to maintain the concentration of bisphenol A in the reaction mixture in the range of 10 to 25% by weight and also to maintain the reaction temperature in the range of from saturated dissolution temperature of bisphenol A $-10°$ C. to said saturated dissolution temperature $+10°$ C., and a discharge line for the reaction mixture, comprising the steps of inputting to a computer, through a detector and a signal circuit which are mounted on the production system, operating conditions on (1) flow rates of the raw materials, catalyst and circulating liquid which are fed to the continuous-flow type reactor and composition of said circulating liquid and (2) level and temperature of the reaction mixture in said reactor; estimating (3) the composition of the reaction mixture, saturated solubility of bisphenol A and slurry concentration of bisphenol A-phenol adduct in said reactor through a calculating mechanism of the computer; (4) comparing these estimates with prescribed set points; and thereby controlling the rate of feeding the raw materials and catalyst to said reactor and the rate of discharging the reaction mixture from said reactor so as to prevent crystallization of said adduct in said reactor, or so as to prevent increase in the slurry concentration exceeding the prescribed level.

2. A preparation process of bisphenol A from phenol and acetone in the presence of hydrogen chloride as an acid catalyst with a production system which includes a continuous-flow type reactor equipped with lines for individually feeding raw materials, catalyst and circulating liquid, means for controlling the temperature of the interior and jacket of the reactor by controlling the process conditions so as to maintain the concentration of bisphenol A in the reaction mixture in the range of 10 to 25% by weight and also to maintain the reaction temperature in the range of from saturated dissolution, temperature of bisphenol A $-10°$ C. to said saturated dissolution temperature $+10°$ C., an external circulation line and heat exchanging means for controlling the reaction mixture by circulating the reaction mixture outside the reactor, and a discharge line for the reaction mixture, comprising the steps of inputting to a computer, through a detector and a signal circuit which are mounted on the production system, operating conditions on (1) flow rates of the raw materials, catalyst and circulating liquid which are fed to the continuous-flow type reactor and composition of said circulating liquid, (2) level and temperature of the reaction mixture in said reactor, and additionally (3) flow rate and temperature of cooling water which is fed to said heat exchanger and of the reaction mixture which is circulated to said heat exchanger; estimating (4) the composition of the reaction mixture, saturated solubility of bisphenol A and slurry concentration of bisphenol A-phenol adduct in said reactor and said heat exchanger through a calculating mechanism of the computer; (5) comparing these estimates with prescribed set points; thereby controlling the rate of feeding the raw materials and catalyst to said reactor and the rate of discharging the reaction mixture from said reactor so as to prevent crystallization of said adduct in said reactor or so as to prevent increase in the slurry concentration exceeding the prescribed level; and controlling the heat-removing rate from the heat exchanger so as to maintain the temperature of the reaction mixture above the saturated solubility temperature of bisphenol A.

3. A preparation process of bisphenol A from phenol and acetone in the presence of hydrogen chloride as an acid catalyst with a production system which includes (1) a batch type reactor equipped with a feed line of a reaction mixture containing bisphenol A which is formed by reaction of phenol with acetone and discharged from a continuous-flow type reactor by controlling the process conditions so as to maintain the concentration of bisphenol A in the reaction mixture in the range of 10 to 25% by weight and also to maintain the reaction temperature in the range of from saturated dissolution temperature of bisphenol A $-10°$ C. to said saturated dissolution temperature $+10°$ C., means for controlling the interior temperature and a level gauge on the reactor, a feed line for purge phenol for the level gauge, and a discharge line for the reaction mixture, (2) a buffer tank equipped with lines for individually feeding the reaction mixture discharged from said batch type reactor, washing phenol and purge phenol for a level gauge, and (3) a dehydrochlorination column equipped with a line for transfer-feeding the reaction mixture in said buffer tank and a line for feeding additional phenol, comprising the steps of (1) inputting to a computer, through a detector and a signal circuit which are mounted on the production system, composition and temperature of a mixture of raw materials which are fed to said batch type reactor; (2) calculating time dependent variation of the reaction mixture composition in said reactor with a numerical integration method; (3) estimating the composition of the reaction mixture and slurry concentration of bisphenol A-phenol adduct at the end of the reaction through a calculating mechanism of the computer; (4) comparing these estimates with prescribed set points; and thereby controlling the concentration of said slurry by adjusting the flow rate of additional phenol so as to stabilize the composition of said reaction mixture of the concentration of said slurry which is continuously fed from a reaction step to a dehydrochlorination step.

4. A preparation process of bisphenol a from phenol and acetone in the presence of hydrogen chloride as an acid catalyst with a production system which incudes (1) a continuous-flow type reactor equipped with lines for individually feeding raw materials, catalyst and circulating liquid, means for controlling the interior and jacket temperatures of the reactor by controlling the operation conditions so as to maintain the concentration of bisphenol A in the reaction mixture in the range of 10 to 25% by weight and also to maintain the reaction temperature in the range of from saturated dissolution temperature of bisphenol A $-10°$ C. to said saturated dissolution temperature $+10°$ C., and a discharge line for the reaction mixture, (2) a batch type reactor equipped with a feed line for the reaction mixture containing bisphenol A which is formed by reaction of phenol with acetone and discharged from the continuous-flow type reactor, means for controlling the interior temperature and a level guage on the reactor, a feed line for purge phenol for the level guage, and a discharge line for the reaction mixture, (3) a buffer tank equipped with lines for individually feeding the reaction mixture discharged from said batch type reactor, washing phenol and purge phenol for a level guage, and (4) a dehydrochlorination column equipped with a line for transfer-feeding the reaction mixture in said buffer tank and a line for feeding additional phenol, comprising a first step of inputting to a computer, through a detector and a signal circuit which are mounted on the production system, operating conditions on (1) flow rates of the raw materials, catalyst and circulating liquid which are fed to the continuous-flow type reactor and composition of said circulating liquid and (2) level and temperature of the reaction mixture in said reactor, and (3) temperature of the reaction mixture in the batch reactor; estimating (4) the composition of the reaction mixture, saturated solubility of bisphenol A and slurry concentration of bisphenol A-phenol adduct in the continuous-flow type reactor through a calculating mechanism of the computer; (5) comparing these estimates with prescribed set points; and thereby controlling the rate of feeding the raw materials and catalyst to said reactor and the rate of discharging the reaction mixture from said reactor so as to prevent crystallization of said adduct in said reactor, or so as to prevent increase in the slurry concentration exceeding the prescribed level; and further comprising a second step of (6) inputting to the computer the temperature of the reaction mixture in said batch type reactor; (7) calculating time dependent variation of the reaction mixture composition in said reactor with a numerical integration method; (8) estimating the composition of the reaction mixture and slurry concentration of bisphenol A-phenol adduct at the end of the reaction in said reactor through a calculating mechanism of the computer; (9) comparing these estimates with prescribed set points; and thereby controlling the concentration of said slurry by adjusting the flow rate of additional phenol so as to stabilize the composition of said reaction mixture or the concentration of said slurry which is continuously fed from a reaction step to a dehydrochlorination step.

5. A preparation process of bisphenol A from phenol and acetone in the presence of hydrogen chloride as an acid catalyst with a production system which includes (1) a continuous-flow type reactor equipped with lines for individually feeding raw material, catalyst and circulating liquid, means for controlling the interior and jacket temperatures of the reactor by controlling the operation conditions so as to maintain the concentration of bisphenol A in the reaction mixture in the range of 10 to 25% by weight and also to maintain the reaction temperature in the range of from saturated dissolution temperature of bisphenol A $-10°$ C. to said saturated dissolution temperature $+10°$ C., an external circulation line and heat-exchanging means for circulating and cooling the reaction mixture outside the reactor, and a discharge line for the reaction mixture (2) a batch type reactor equipped with a feed line for the reaction mixture containing bisphenol A which is formed by reaction of phenol with acetone and discharged from the continuous-flow type reactor, means for controlling the interior temperature and a level gauge on the reactor, a feed line for purge phenol for the level gauge, and a discharge line for the reaction mixture, (3) a buffer tank equipped with lines for individually feeding the reaction mixture discharged from said batch type reactor, washing phenol and purge phenol for a level gauge and (4) a dehydrochlorination column equipped with a line for transfer-feeding the reaction mixture in said buffer tank and a line for feeding additional phenol, comprising a first step of inputting to the computer, through a detector and a signal circuit which are mounted on the production system, operating conditions on (1) flow rates of the raw materials, catalyst and circulating liquid which are fed to the continuous-flow type reactor and composition of said circulating liquid, (2) level and temperature of the reaction mixture in said reactor, and (3) feeding rate and temperature of cooling water which is fed to said heat exchanger and of the reaction product which is circulated to said heat exchanger; estimating (4) the composition of the reaction mixture, saturated solubility of bisphenol A and slurry concentration of bisphenol A-phenol adduct in said reactor and said heat exchanger through a calculating mechanism of the computer; comparing (5) these estimates which prescribed set points; and thereby controlling the rate of feeding the raw materials and catalyst to said reactor and the rate of discharging the reaction mixture from said reactor so as to prevent crystallization of said adduct in said reactor, or so as to prevent increase in the slurry concentration exceeding the prescribed level, and further controlling the heat-removing rate from said heat exchanger so as to maintain the temperature of the reaction mixture above the saturated solubility temperature or supersaturated solubility temperature of bisphenol A; and comprising a second step of (6) inputting to the computer the temperature of the reaction mixture in said batch type reactor; (7) calculating time dependent variation of the reaction mixture composition in said reactor with a numerical integration method; (8) estimating the composition of the reaction mixture and slurry concentration of bisphenol A-phenol adduct at the end of the reaction through a calculating mechanism of the computer; (9) comparing these estimates with prescribed set points; and thereby controlling the concentration of said slurry by adjusting the feeding rate of additional phenol so as to stabilize the composition of said reaction mixture or the concentration of said slurry which is continuously fed from a reaction step to a dehydrochlorination step.

* * * * *